US012098386B2

(12) United States Patent
Sellathurai et al.

(10) Patent No.: US 12,098,386 B2
(45) Date of Patent: Sep. 24, 2024

(54) USE OF GERM CELLS FOR PREPARING A MICRO HAIR FOLLICLE

(71) Applicant: L'OREAL, Paris (FR)

(72) Inventors: Theebah Sellathurai, Aulnay-sous-Bois (FR); Khalid Bakkar, Aulnay-sous-Bois (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/462,346

(22) PCT Filed: Dec. 13, 2017

(86) PCT No.: PCT/EP2017/082548
§ 371 (c)(1),
(2) Date: May 20, 2019

(87) PCT Pub. No.: WO2018/114504
PCT Pub. Date: Jun. 28, 2018

(65) Prior Publication Data
US 2020/0181571 A1 Jun. 11, 2020

(30) Foreign Application Priority Data
Dec. 23, 2016 (FR) ...................... 1663324

(51) Int. Cl.
C12N 5/071 (2010.01)
C12N 5/0775 (2010.01)

(52) U.S. Cl.
CPC ......... C12N 5/0628 (2013.01); C12N 5/0666 (2013.01); C12N 5/0697 (2013.01); C12N 2501/40 (2013.01); C12N 2501/727 (2013.01); C12N 2501/999 (2013.01); C12N 2502/092 (2013.01); C12N 2502/094 (2013.01); C12N 2502/13 (2013.01); C12N 2502/1376 (2013.01); C12N 2513/00 (2013.01)

(58) Field of Classification Search
CPC .. C12N 5/0628; C12N 5/0666; C12N 5/0697; C12N 2502/094; C12N 2502/13; C12N 2501/999; C12N 2501/40; C12N 2502/092; C12N 2502/1376; C12N 2513/00
See application file for complete search history.

(56) References Cited

U.S. PATENT DOCUMENTS

| 2005/0089512 | A1  | 4/2005  | Schlotmann |
| 2008/0097607 | A1  | 4/2008  | Bakkar et al. |
| 2011/0086079 | A1* | 4/2011  | Lindner ............. A61P 17/14 424/422 |
| 2011/0686679 |     | 4/2011  | Lindner et al. |
| 2012/0269781 | A1* | 10/2012 | Ra ..................... A61P 17/14 424/93.7 |
| 2014/0370070 | A1  | 12/2014 | Lindner |

FOREIGN PATENT DOCUMENTS

| CN | 101385871 A     | 3/2009  |
| CN | 102712896 A     | 10/2012 |
| EP | 1 878 790 A1    | 1/2008  |
| EP | 2 274 419 A1    | 1/2011  |
| WO | WO 95/01423 A1  | 1/1995  |
| WO | WO 2007/109223 A2 | 9/2007 |
| WO | WO-2011/056017 A2 | 5/2011 |

OTHER PUBLICATIONS

Yang et al. Upper Human Hair Follicle Contains a Subpopulation of Keratinocytes with Superior In Vitro Proliferative Potential. J. Invest. Dermatol. 101:652-659 (Year: 1993).*
Lavker et al. Hair Follicle Stem Cells. JID Symposium Proceedings 8:28-38 (Year: 2003).*
Blanpain et al. Self-Renewal, Multipotency, and the Existence of Two Cell Populations within an Epithelial Stem Cell Niche. Cell, vol. 118, 635-648 (Year: 2004).*
Roh et al. Dermal papilla-induced hair differentiation of adult epithelial stem cells from human skin. Physiol Genomics 19: 207-217 (Year: 2004).*
Roh et al. In Vitro Differences Between Keratinocyte Stem Cells and Transit-Amplifying Cells of the Human Hair Follicle. J Invest Dermatol 125:1099-1105 (Year: 2005).*
Chacon-Martinez et al. Hair follicle stem cell cultures reveal self-organizing plasticity of stem cells and their progeny. The EMBO Journal (2017) 36: 151-164 (Year: 2017).*
Inoue et al. Differential expression of stem-cell-associated markers in human hair follicle epithelial cells. Laboratory Investigation (2009) 89, 844-856 (Year: 2009).*
Hilmi et al. A simple culture method for epithelial stem cells derived from human hair follicle. Cent. Eur. J. Biol. 8(5):432-439 (Year: 2013).*
Horland et al., "Human hair follicle equivalents in vitro for transplantation and chip-based substance testing", BMC Proceedings, 2011, vol. 5 (Supp. 8), 1753-6561.
Lindner et al., "De novo formation and ultra-structural characterization of a fiber-producing human hair follicle equivalent in vitro", Journal of Biotechnology, Nov. 22, 2011,152, 108-112.
Blanpain et al., "Self-renewal, multipotency, and the existence of two cell populations within an epithelial stem cell niche", CELL, Sep. 3, 2004, vol. 118, 635-648.
Balana, "Epidermal stem cells and skin tissue engineering in hair follicle regeneration", World Journal of Stem Cells, May 26, 2015, vol. 7, No. 4, 711-727.
Ohyama et al., "Hair follicle bulge: A fascinating reservoir of epithelial stem cells", Journal of Dermatological Science, 2007, vol. 46, No. 2, 81-89.

(Continued)

Primary Examiner — Taeyoon Kim
(74) Attorney, Agent, or Firm — POLSINELLI PC

(57) ABSTRACT

The invention relates to the use of germ cells for obtaining a micro hair follicle and to the use thereof for evaluating the effect of cosmetic, pharmaceutical or dermatological products and also for the prophylactic or therapeutic treatment of a state of reduced pilosity.

12 Claims, 8 Drawing Sheets

(56) References Cited

OTHER PUBLICATIONS

Yang et al., "Review of hair follicle dermal cells", Journal of Dermatological Science, 57 (2010) 2-11.
Thibaut et al., "Hair keratin pattern in human hair follicles grown in vitro", Experimental Dermatology 2003, 12: 160-164.
Mahjour et al., Tiss. Eng. B, 18(1): 15-23, 2012.
Moll et al., Histochem. Cell Biol., 129:705-733, 2008.
Duchstein et al., Chem. Chem. Phys., 17:21880-21884, 2015.
Hirobe, Dermatol. Sinica, 32:200-204, 2014.
Vogt et al., Hair Growth and Disorders, Chapter 1, 2008.
Guo et al., Cell. Reprog., 17(1):77-87, 2014.
Hwang et al., Develop., 135(18):3149-3159, 2008.
Rogers et al., Int. J. Dev. Biol. 48: 163-170, 2004.
Sasahara et al., Int. J. Oncol., 34:1191-1199, 2009.
Wagner et al., BMC Proceedings, 7(6):p. 93, 2013.
Yao Wang, "Experimental study on the multi-lineage differentiation potential of hair follicle stem cells and their differentiation into sweat glad cells," Chinese Doctoral Dissertations Full-text Database, issue 6, 2014. See Attachment for a Discussion Wang.

* cited by examiner

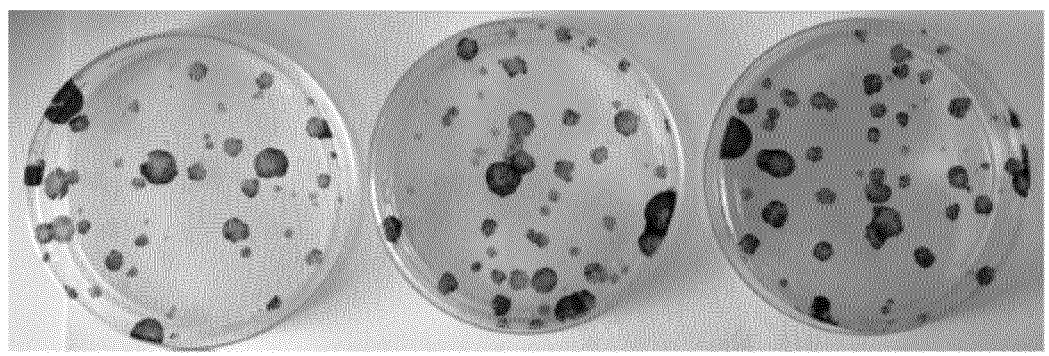
Figure 7a)
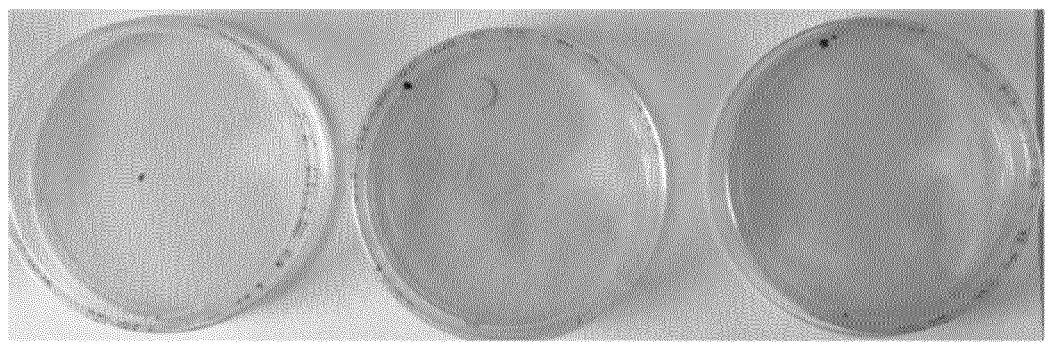
Figure 7b)
Figure 7

USE OF GERM CELLS FOR PREPARING A MICRO HAIR FOLLICLE

CROSS REFERENCE TO RELATED APPLICATIONS

This application is a National Phase filing under 35 U.S.C. § 371 of PCT/EP2017/082548 filed on Dec. 13, 2017; which application in turn claims priority to Application No. 1663324 filed in France on Dec. 23, 2016. The entire contents of each application are hereby incorporated by reference.

The present invention relates to an "in vitro" process for producing a micro hair follicle by culture and amplification of germ cells.

It likewise relates to the micro hair follicles produced by means of the process mentioned above and to the use thereof for treating alopecia and also for evaluating the effect of cosmetic, pharmaceutical and dermatological products.

Alopecia is conditioned by various factors: genetic, hormonal and environmental, by the diet and by physical activity. The hair has an essential aesthetic and identity role. Alopecia in women or in men can thus be responsible for considerable psychological suffering.

Thus, healthy, strong hair and a dense head of hair throughout one's lifetime is an ambition of most women and men.

Many techniques are known for treating alopecia, such as cell therapy, laser therapy or else implants without surgery. The latter gives an immediate result and is much less invasive than surgery.

In order to obtain implants, human hair follicles are obtained by culturing various cell types present in the hair bulb.

The hair bulb is pear-shaped and it is composed:
of the papilla which is a budding of dermal origin, located at the base of the follicle. It is a highly vascularized site which participates in the nutrition and regulation of the growth of the hair through its store of growth factors and extracellular matrix proteins;
of the matrix which is a zone capping the dermal papilla, constituted of a clump of matrix cells which are not very differentiated. It is the seat of intense mitotic activity. The matrix cells, which are located in the hair bulb and which form a small cell clump around the dermal papilla, are mainly constituted of precursors of keratinocytes which constitute a germinative stratum and which proliferate rapidly so as to differentiate to form the hair shaft, thus playing an essential role in the hair cycle. From the beginning of the anagen phase up to the end of said phase, these matrix cells will proliferate up to the catagen phase and then disappear in the telogen phase. (Ebling F J. The biology of hair. Dermatol Clin. 1987 July; 5(3):467-81. Review; Saitoh M, Uzuka M, Sakamoto M. Human hair cycle. J Invest Dermatol. 1970, January 54, pages 65-32. Cell differentiation will allow the formation of the various cell types of the outer epithelial sheath (ORS), of the inner epithelial sheath (IRS) and then of the hair shaft. It is also this matrix which conditions the shape of the hair. The matrix is distributed uniformly about an axis of symmetry for straight hair, whereas it will be greater on one side for curly hair (Voyage 3D au Coeur du cheveu [3D voyage to the Heart of the hair] web site—URL: www.hair-science.com; Melissopoulos A and Levacher C. Les annexes cutanées [The skin appendages]. In: La peau: structure et physiologie [The skin: structure and physiology], published by Lavoisier; 1998. P. 57-99). The matrix also comprises follicle melanocytes which are responsible for the pigmentation of the hair. The proliferation and differentiation of these matrix cells are controlled by the dermal papilla (Botchkarev V A, Kishimoto J. Molecular control of epithelial-mesenchymal interactions during hair follicle cycling. J Invest Dermatol Symp Proc. 2003 June; 8(1):46-55. Review);
of the outer and inner epithelial sheaths which are produced by the upper matrix of the hair bulb, also known as the keratinization zone. The outer epithelial sheath constitutes the outer envelope of the follicle: it is an invagination of the epidermis. It houses in particular stem cells from which the hair follicle will be cyclically regenerated. The inner epithelial sheath separates the outer epithelial sheath from the hair shaft. This sheath is constituted of three cell types organized in keratinized concentric layers which accompany the growth of the hair. Henlé's layer, Huxley's layer and the cuticle which is formed from flattened cells, directed towards the hair matrix, are distinguished;
of the hair shaft which is partly visible, this is the hair. The structure of the hair shaft is made up of three distinct layers from the outside to the inside. There is the cuticle, the cortex and the medulla, all made up all keratinized cells.

In its lifetime, the hair goes through three phases of development of very unequal durations:
The anagen phase is the active phase of the hair, the one during which it lives and grows regularly. It lasts from 4 to 7 years. The germ cells which surround the papilla of the hair root bulb continually produce the material which allows the hair to live and grow. Next, the multiplication of the germ cells stops at the bottom of the follicle. The active phase of the hair is then ended; another begins, which is much shorter.
The catagen phase: In barely 15 days, the hair bulb disappears (since it is no longer fed because of the interruption of the germinative cells) and becomes transformed at an accelerated speed. The papilla disappears, that is to say that the hollow bulb becomes solid; it keratinizes, hardens and becomes cornified. The hair is then dead; the follicle tightens so as to expel the dead hair.

The telogen phase is the phase which lasts approximately three months and during which the dead hair is waiting to fall out. In order to fall out, the hair must be pushed out by the new hair which in turn grows in the same follicle and which will expel the old hair.

The regeneration of the hair follicle then takes place starting from the stem cells, called germ cells, located in the "bulge".

The "bulge" is formed by a cell subpopulation of the outer epithelial sheath, called germ cells, located in the middle portion of the hair follicle, and more exactly in the hair arrector muscle insertion zone. These cells represent the lowest part of the permanent portion of the follicle.

In the "bulge", the keratinocytes are relatively undifferentiated, biochemically and ultra-structurally.

This "bulge" is in a strategic position to interact during the late telogen phase, with the ascendant dermal papilla, and to initiate a new follicle in anagen. The germ cells are thus cells that are essential for renewal of the hair. The germ cells (germinative cells or pluripotent cells or stem cells) of the telogen hair are involved in the exiting of the hair follicle from the dormant phase and therefore regrowth of the hair.

For the purposes of the invention, the term "germ cells" is intended to mean the stem cells present in the "bulge".

For several years, hair follicle cells from the compartments that are easy to access by micro-dissection have been cultured, EP 2 274 419, EP 2 447 357.

However, dissection of the telogen follicle is particularly difficult, in particular because of its rarity, which represents less than 15% of all the follicles present on the scalp. Dissection of the telogen follicle is furthermore particularly difficult because in particular of its dermal environment. One of the difficulties is thus to obtain the germ cells in sufficient amount to regenerate a hair follicle capable of renewing. The team of S. Lyle, in 2005, carried out a primary culture of these cells by means of an amplification starting from a telogen follicle prepared by digestion with dispase and then pulled out, which does not make it possible to extract all of the germ cells in sufficient amount to place them in culture and to maintain, in vitro, the expression of germ cell-specific markers in order to regenerate a hair follicle (Roh C, Tao Q, Photopoulos C, Lyle S. J Invest Dermatol. 2005, 125: 1099-1105).

Regarding cell therapy, the company Replicel uses connective tissue sheath cells to obtain a fine shaft which is non-pigmented and which does not recycle; because the connective tissue sheath cells will recruit the keratinocytes of the skin (method used by Jahoda, 1999; Higgins, 2013).

None of these models contains germ cells, the presence and the amount of which are essential to the formation of a microfollicle having most of the characteristics of a human microfollicle and in particular its renewal capacity.

Surprisingly, the inventors have succeeded in obtaining germ cells in a sufficient amount so that, when they are brought into contact with dermal papilla fibroblasts and also connective tissue sheath fibroblasts, a tubular structure responsible for a micro hair follicle forms and, because of the presence of the germ cells, is capable of recycling.

Indeed, the applicant has demonstrated that the culture of germ cells in the presence of the Rock Y27632 inhibitor allows considerable proliferation of these cells and the differentiation thereof into keratinocytes that are positive for the CD200, CD29 and K15 markers. It can, moreover, be noted that these cells are small cells, having a high nuclear/cytoplasmic ratio and a homogeneous phenotype.

When these cells are brought into contact with the connective tissue sheath fibroblasts and also the dermal papilla fibroblasts, the formation of a tubular structure that will be responsible for the formation of a micro hair follicle is observed.

The mixing of the cells obtained with connective tissue sheath fibroblasts and also the fibroblasts of the dermal family placed in 3D culture makes it possible to obtain, unexpectedly, the formation of a bud from the mixed spheroids constituted of the germ cells and of the dermal papilla fibroblasts and also the connective tissue sheath fibroblasts. This budding is in the form of a tubular structure that will be responsible for the formation of the hair follicle.

For the purposes of the invention, the term "tubular structure" is intended to mean a budding which forms from the mixed spheroids.

For the purposes of the invention, the term "mixed spheroids" is intended to mean the 3D culture of the germ cells and of the dermal papilla fibroblasts and also the connective tissue sheath fibroblasts.

For the purposes of the invention, the term "tubular structure" is intended to mean the budding observed after 3D culture of the germ cells and of the dermal papilla fibroblasts or the connective tissue sheath fibroblasts. This tubular structure constituted, on the one hand, of the epithelial stem cells of the hair and, on the other hand, of the mesenchymal cells of the hair will be responsible for the formation of the micro follicle.

The process, according to the invention, therefore proves to be advantageous because it makes it possible to obtain a hair follicle using the fibroblasts of the hair and germ cells required for the formation of a hair follicle having most of the characteristics of a human microfollicle and in particular capable of regenerating.

Thus, according to a first of its subjects, the present invention relates to the use of germ cells for obtaining a hair follicle.

Use of Germ Cells for Preparing a Micro Hair Follicle

The germ cells may be sampled according to the process which follows: hair follicles in the telogen phase are placed in a Petri dish containing a minimum culture medium supplemented with 2% of antibiotic and non-essential amino acids.

The region of the germ cells, called the bulge, is extracted from the connective tissue sheath and then placed in a petri dish containing a feeder layer of 3T3i fibroblasts.

In order to obtain a sufficient amount of germ cells for obtaining a micro hair follicle, the applicant has developed a method of amplifying these cells so that they differentiate into CD200, CD29 and K15 keratinocytes.

Thus, the applicant has developed a process for preparing a micro hair follicle, comprising at least one step of amplifying the germ cells in the presence of an effective amount of a ROCK inhibitor for a period of time sufficient to allow differentiation of said cells into keratinocytes positive for the CD200, CD29 and K15 markers.

This process for preparing the micro hair follicle is characterized in that it comprises the following steps:
 a—isolating a hair follicle in the telogen phase from a scalp sample;
 b—separating the germ cells from the connective tissue sheath;
 c—depositing the cell aggregate on a feeder layer of 3T3i fibroblasts, that have been irradiated or blocked with mitomycin, in a Green 7F medium;
 d—amplifying the germ cells at the surface of said support in the presence of a ROCK inhibitor;
 e—recovering the keratinocytes exhibiting the CD200, CD29 and K15 markers;
 f—culturing the keratinocytes obtained in step e) in 3D culture in the presence of fibroblasts from the connective tissue sheath and/or from the dermal papilla.

The culturing of the germ cells in 3D culture in the presence of fibroblasts from the connective tissue sheath and/or from the dermal papilla makes it possible to obtain a hair structure responsible for the micro hair follicle, capable of renewing by virtue of the presence of the germ cells.

The micro hair follicle obtained from the culture of the germ cells is therefore capable of renewing.

In particular, the micro hair follicle obtained from the culture of the germ cells in the presence of fibroblasts from the connective tissue sheath and/or from the dermal papilla is capable of renewing.

Microdissection

One of the difficulties to be overcome lies in the obtaining of hair follicles in the telogen phase by microdissection.

This is because, under normal conditions, when a hair falls out, the bulge compartment containing the stem cells called germ cells will make it possible to initiate the development of a new hair cycle and will again give a new follicle.

Thus, pulling out a telogen hair does not make it possible to obtain these germ cells; it will therefore be necessary to perform a scalp biopsy, and then to isolate these cells by microdissection.

According to the invention, the germ cells are obtained by means of a novel microdissection technique which preserves the amount and the integrity of the cells, since they are not separated from one another. Indeed, the hair in the telogen phase is isolated on a support, and the telogen shaft containing the germ cells located in the bulge is extracted. This microdissection makes it possible to isolate and preserve all of the germ cells.

For the purposes of the invention, the term "telogen" is intended to mean the follicle which contained the hair in the telogen phase.

Amplification

In addition to being difficult to isolate, the germ cells are also difficult to culture at least for the following reasons:
a) the number thereof is particularly low;
b) they are difficult to amplify.

The applicant has isolated the germ cells and developed a process for culturing these cells. Specifically, in the presence of the Y27632 growth factor, which is a ROCK inhibitor, these cells proliferate rapidly and differentiate into CD200, CD29 and K15 keratinocytes until they reach confluence. The process makes possible recovery of the keratinocytes positives for the CD200, CD29 and K15 markers when they reach confluence while forming regular clusters.

The cells are amplified according to the technique of Rheinwald and Green (Cell, vol. 6, 331-344, 1975) by culturing on a feeder support constituted of fibroblasts in a suitable medium known to those skilled in the art, in the presence of growth factors, in particular amino acids, serum, cholera toxin, insulin, triiodothyronine and pH buffer solution. In particular, such a culture medium may in particular contain at least one mitogenic growth factor for keratinocytes (for example epidermal growth factor (EGF) and/or keratinocyte growth factor (KGF), in particular KGF), insulin, hydrocortisone and optionally an antibiotic (e.g.: gentamycin, amphotericin B) to which a ROCK inhibitor, Y27632, has been added.

Advantageously, said medium may also comprise serum or a pituitary extract, for example of bovine origin, epinephrine, transferrin and/or non-essential amino acids.

The fibroblasts used for this culture will more preferentially be 3T3 fibroblasts. 3T3 fibroblasts are well known to those skilled in the art. It is a fibroblast cell line that has been known since 1962. "3T3" means "3-day transfer, inoculum of $3 \times 10^5$ cells".

The cell culture is preferably a culture on fibroblasts (preferentially 3T3 fibroblasts), the proliferation of which has been stopped beforehand, preferentially by having previously irradiated them (for example with gamma radiation) or previously treated them with mitomycin. Mitomycin (in particular mitomycin C) blocks the proliferation of these cells without however preventing them from producing nutritive substances useful for keratinocyte proliferation.

With this technique, the germ cells proliferate on the support on which they have been separated from the other cell types. This makes it possible to preserve a sufficient number of germ cells. The cells proliferate rapidly in the presence of Y27632 up to confluence and differentiate into cells that are positive for the markers CD200, CD29 and K15.

According to the invention, the term "effective amount" denotes an amount required to obtain a culture of CD200, CD29 and K15 keratinocytes at confluence.

According to the invention, the effective amount of the ROCK inhibitor, Y27632, is between 1 and 100 µM and preferably between 5 and 25 µM and preferably 10 µM.

According to the invention, the germ cells are cultured in the presence of the ROCK inhibitor, Y27632, for at least 2 days and preferably for at least 3 days.

Preferably, the cells are placed in culture in a cell number of between 1000 and 4000 cells and preferably in a number of 3000 cells per $cm^2$.

The term "at confluence" is intended to mean a cell layer having no interstice between each adherent cell cultured in monolayer on an appropriate support, such as a culture dish.

Culturing of CD200, CD29, K15 Cells in 3D Culture to Obtain Micro Hair Follicles The 3D spheres are obtained by seeding the cells on 96-well microplates of Insphero type by the hanging drop method or method with microplates for culturing non-adherent cells (GravityPLUS White paper system).

The germ cells and the fibroblasts from the connective tissue sheath and/or the dermal papilla are then cultured in a green medium at 37° C.; the appearance of the micro hair follicle is observed after at least 3 days of culture.

According to one embodiment, the cells are maintained in culture for at least 3 days and preferably at least 5 days.

Preferably, the number of cells placed in culture is between 1000 and 4000 cells and is preferably 3000 cells per $cm^2$.

Another subject of the invention is a micro hair follicle that can be obtained by means of the process according to the invention.

These micro hair follicles make it possible on the one hand to use them for the prophylactic or therapeutic treatment of a state of reduced pilosity, in particular alopecia, and constitute on the other hand predictive tests for the activity of cosmetic and/or pharmaceutical active agents or else side effects of topical ingredients.

Prophylactic or Therapeutic Treatment of a State of Reduced Pilosity, in Particular Alopecia Given that the micro hair follicle has the characteristics of a hair follicle in vivo, it may be used as an implant, optionally combined with skin substitutes.

The micro hair follicle according to the invention will therefore also have uses for preparing implants and/or a skin substitute for treating a skin disorder such as a burn, a healing defect or hair that has turned white or grey.

A therapeutic effect is defined as a return to the normal state of pilosity, whether totally or partially.

For the purposes of the invention, prophylactic treatment is recommended if the subject has a prior condition for hair loss, such as a familial disposition.

The conditions of a reduced amount of hair may be the result of alopecia, hereditary baldness, scars, burns or accidental injuries.

Predictive Tests for the Activity of Cosmetic and/or Pharmaceutical Active Agents The micro hair follicle equivalents according to the invention make it possible to perform in particular time courses of body hair or head hair growth and therefore any study requiring numerous hairs that are alive and as complete as possible in an in vivo context such as the study of the hair cycle and of the factors capable of influencing this cycle, ranging up to the study of active agents which promote hair growth, of active agents which make it possible to combat hair loss or else of active agents which slow down body hair growth.

The product screening processes for the purpose of identifying novel active agents comprise a step (a) of bringing said test product into contact with a micro hair follicle according to the invention, then a step (b) of analysing the effect of said product on at least one parameter of the micro hair follicle and a step (c) of selecting the product which modifies said parameter.

Preferably, for carrying out step (a), the test product is applied topically, for example, formulated in conventional topical formulations or else introduced into the culture medium.

Step (b) may, in particular, be carried out by analysing the expression, the production and/or the activity of markers associated with the quality and/or with the homeostasis of the micro hair follicle, for instance follicle markers for the structural proteins. As an example of structural proteins, mention may be made of the hair keratins.

For this, the effect of the product on the growth of the hair shaft will be analysed in step (b) of the screening process.

Step (b) of analysing the effect of the product will preferentially be a comparison of at least one parameter measured on the micro hair follicle according to the invention brought into contact with the test product with that or those measured on a control micro hair follicle cultured under the same conditions but which has not received the test product.

Step (c) of selecting the product which modifies the parameter of the micro hair follicle will be carried out as a function of a criterion determined beforehand.

The modification of this parameter may be a stimulation, a decrease or a total or partial inhibition of the expression, of the production and/or of the activity of markers and/or of the growth of the hair shaft.

The criterion for selecting said product will for example be that this product has a stimulatory or inhibitory effect on the parameter measured.

The micro hair follicle according to the invention can also be used in automated processes for screening cosmetic, pharmaceutical or dermatological compounds for identifying novel active agents.

DESCRIPTION OF THE FIGURES

The figures make it possible to give a better illustration of the invention, without however limiting the scope thereof.
FIG. 7: Proliferation of the germ cells with Rock inhibitor (FIG. 7a) and without Rock inhibitor (FIG. 7b)

The examples given below are presented as non-limiting illustrations of the invention.

EXAMPLE 1—PREPARATION OF GERM CELLS

Experimental Protocol

Figure 1:
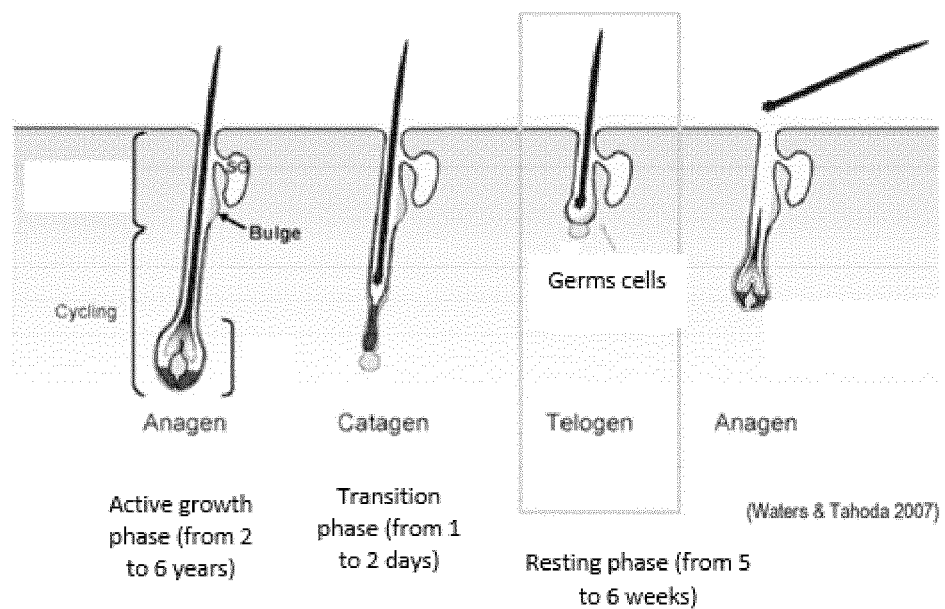
FIG. 1: Germ cell localization
Figure 2:
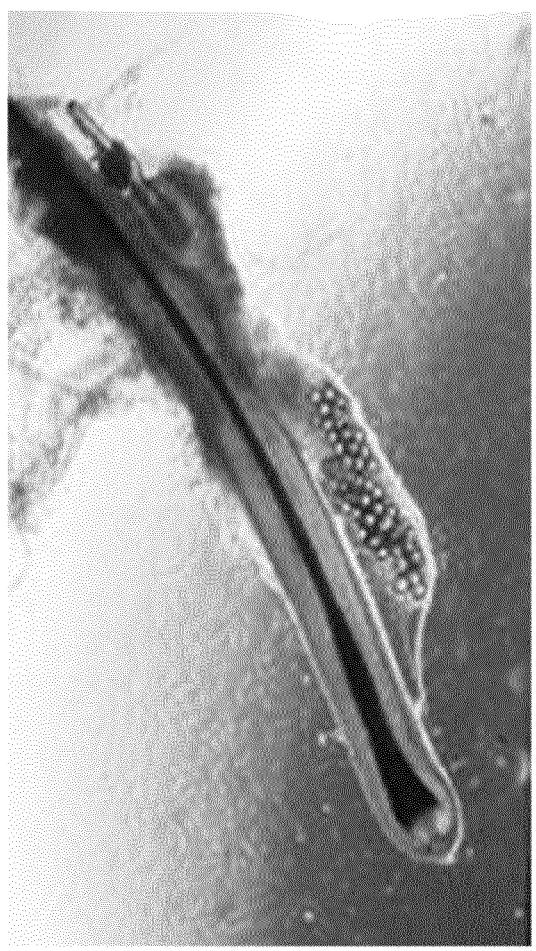
FIG. 2: Separation of the connective tissue sheath cells and of the germ cells with a needle
Figure 3:
FIG. 3: Isolation of a telogen follicle containing the germ cells

The germ cell region, called the bulge (FIG. 1), is extracted from the connective tissue sheath (FIG. 2) and then placed in a petri dish containing 3T3i cells (FIG. 3).

i. Germ Cell Microdissection

The hair follicles are extracted from a surgical residue of scalp. Said residue is first cut into 5 mm$^2$ portions and then sectioned using a scalpel between the dermis and the hypodermis.

The follicles are extracted using ophthalmic surgery forceps and are then sectioned just above the papilla with a scalpel. The bulb is then recovered. At this stage, the bulb comprises two compartments: the dermal compartment (dermal papilla and connective tissue sheath) and the matrix cells which form a cell mass.

The epithelial part is separated from the dermal part using perfusion needles. Only the epithelial part is cultured.

ii. Culture Conditions:

The culture conditions have three main components:
The Base Medium:

Unless otherwise indicated, all of the media and buffers used in the examples are described in Bell et al. 1979, (P.N.A.S. USA, 76, 1274-1278), Asselineau and Prunieras, 1984, (British J. of Derm., 111, 219-222) or Asselineau et al., 1987, (Models in dermato., vol. III, Ed. Lowe & Maibach, 1-7).

The MEM medium+10% FCS+7F (called Green 7F medium) has the following composition:

| MEM | Final concentrations |
|---|---|
| Foetal calf serum (FCS) | 10% |
| L-Glutamine | 2 mM |
| Sodium pyruvate | 1 mM |
| Penicillin - Streptomycin | Penicillin 20 U/ml |
| | Streptomycin 20 µg/ml |
| Fungizone | Penicillin 10 U/ml |
| | Streptomycin 10 µg/ml |
| | Amphotericin-B 25 ng/ml |
| Epidermal growth factor (EGF) | 10 ng/ml |
| Cholera toxin | $10^{-10}$ M |
| Hydrocortisone | 0.4 µg/ml |
| Adenine hydrochloride | $1.8 \times 10^{-4}$ M |
| Triiodothyonine (T3) | $2 \times 10^{-9}$ M |
| Human transferrin | 5 µg/ml |
| Bovine insulin | 5 µg/ml | the culture supplements: growth factors and for instance 10 µM of Y27632.
the adhesion surface: the germ cells proliferate in the Green-based medium in the presence of a feeder layer of murine 3T3 fibroblasts arrested in the cell cycle by mitomycin treatment.

Culture-Amplification of Keratinocytes

After microdissection, the hair follicles in the telogen phase are deposited in Petri dishes 60 mm in diameter, seeded beforehand with 1 million 3T3 cells, and covered with the complete Green 7F culture medium; a culture of germ cells at confluence is obtained.

In order to generate the spheres, the cells are recovered at the subconfluent stage by enzymatic treatment. The spheres can be obtained in various ways with the conventional techniques already described (hanging drop, centrifugation, non-adhesive support). In the case of the hanging drop, 3000 cells are placed in the plates in spheno. They are recovered in 96-well plates after 48 h in order to monitor their progression.

Figure 4:
FIG. 4: Telogen follicle deposited on a feeder layer of 3T3 and migration of the first germ cells around the telogen follicle
Figure 5:
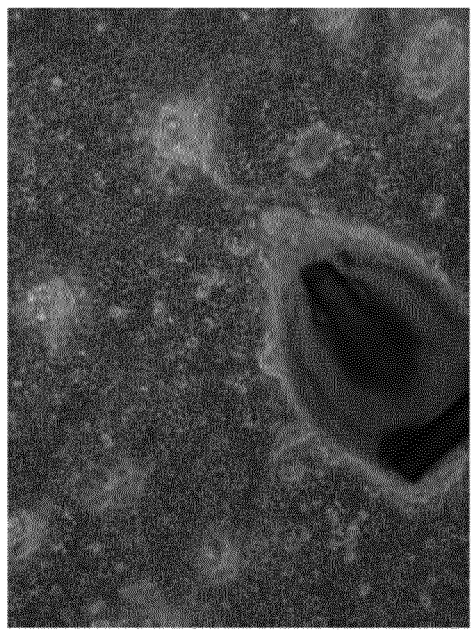
FIG. 5: Germ cells at confluence after 10 days of culture

The telogen hair with the non-dissociated germ cell clump are isolated and deposited on a 3T3 feeder layer (FIG. 3). After 3 d of culture, the cells begin to proliferate in the form of a colony around the germ clump (FIG. 4). The cells reach subconfluence in 7 days (FIG. 5). They are characterized by a very small size and a strong proliferative capacity. In order to ensure amplification, the cells are then seeded into a T75 flask. Thus, after 3 weeks of culture of 3 bulbs, it is possible to generate approximately 40 million germ cells at passage 1.

It was possible to observe that the germ cells are capable of very rapidly reaching confluence in the green 7F medium in the presence of the Rock Y27632 inhibitor at a concentration of 10 μM (FIG. 7a)), whereas, in the same medium without addition of the rock inhibitor, the cells do not proliferate (FIG. 7b)).

Figure 6:
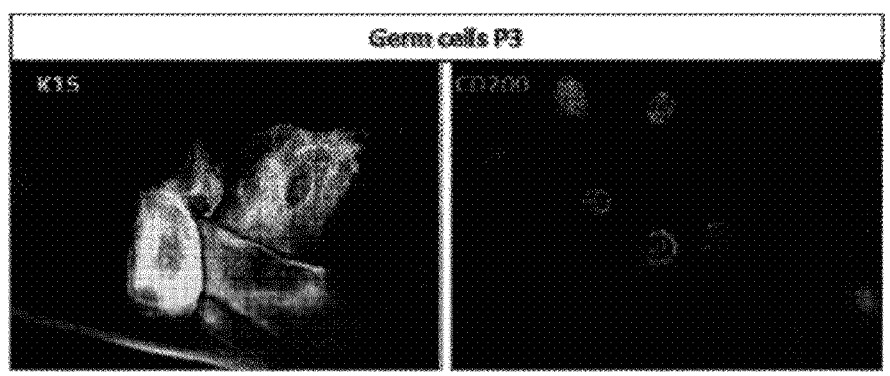
FIG. 6: Characterization of the cells at confluence, K15+, CD29+ and CD200+ keratinocytes
Figure 6:
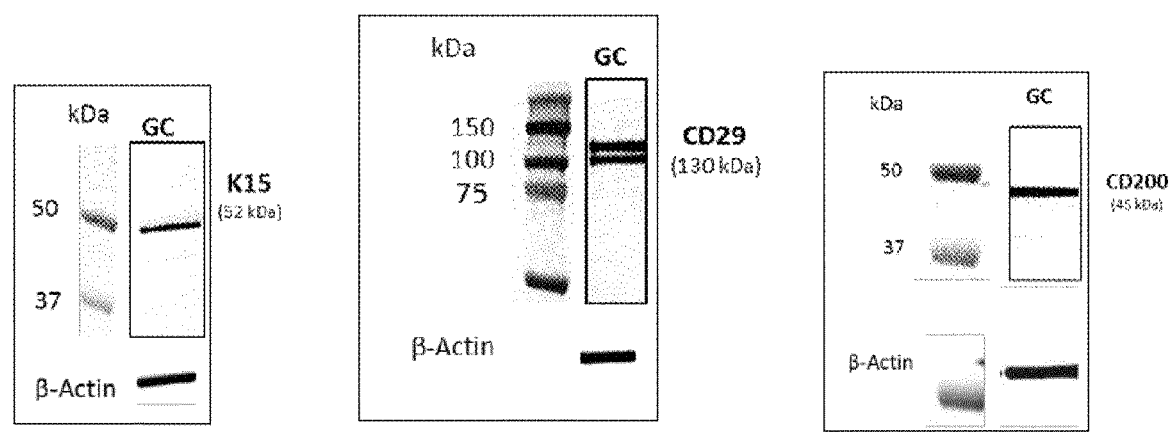
Figure 8:
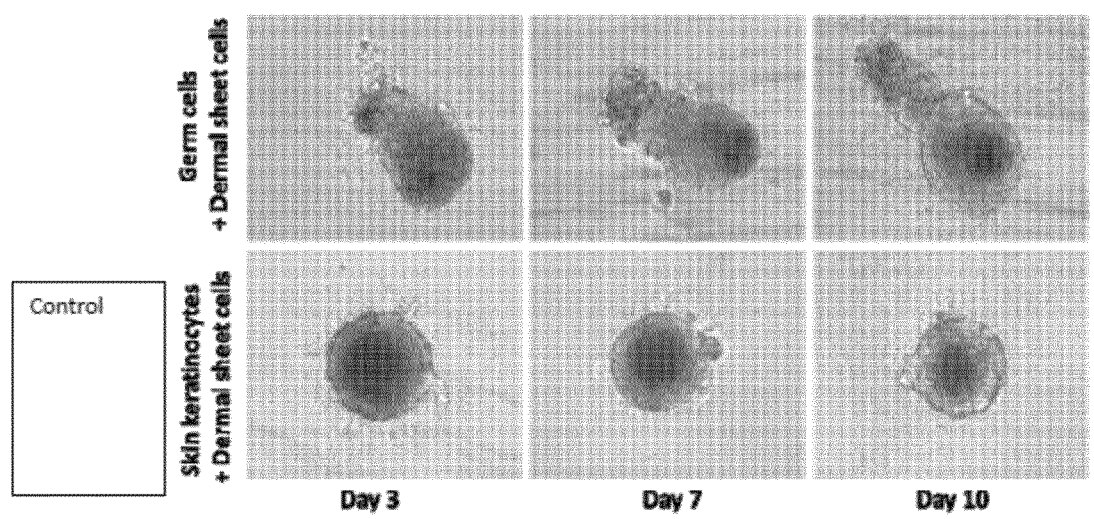
FIG. 8: Formation of the tubular structure responsible for the hair follicle after 3, 7 and 10 days of culture.

Thus, the germ cells cultured in 7F medium containing the rock inhibitor make it possible to obtain keratinocytes that are positive for the K15, CD29 and CD200 markers (FIG. 6) in sufficient amounts. Moreover, these cells are small in size, having a high nuclear/cytoplasmic ratio and a homogeneous phenotype.

The cells which are obtained in a sufficient amount and which have the K15, CD29 and CD200 markers, homogeneously and reproducibly, are then placed in 3D culture in the presence of the fibroblasts from the connective tissue sheath and/or from the dermal papilla. These cells form spheres after 3 d of culture.

After some 3 additional days of culture, these spheres change conformation, showing a polarized organization. A budding appears, which seems to indicate differentiation of the spheres into a tubular structure responsible for the formation of the hair follicle.

The invention claimed is:

1. An in vitro process for preparing a micro hair follicle, comprising amplifying germ cells isolated from the bulge of a hair follicle in the telogen phase to obtain keratinocytes positive for CD200, CD29 and K15 markers in the presence of a ROCK inhibitor and then at least one step of culturing the keratinocytes positive for CD200, CD29 and K15 markers for a period of time sufficient to allow differentiation into a tubular structure of said keratinocytes positive for CD200, CD29 and K15 markers being brought into contact with the connective tissue sheath fibroblasts and/or dermal papilla fibroblasts.

2. The process according to claim 1, wherein the micro hair follicle is capable of renewing.

3. The process according to claim 1, in which the ROCK inhibitor is Y27632.

4. The process according to claim 1, in which an effective amount of the ROCK inhibitor is from 1 to 100 μM.

5. The process according to claim 1, in which an effective amount of the ROCK inhibitor is from 5 to 25 μM.

6. The process according to claim 1, in which the an effective amount of the ROCK inhibitor is 10 μM.

7. The process according to claim 1, in which the germ cells are amplified in the presence of the ROCK inhibitor for at least 2 days.

8. The process according to claim 1, in which the germ cells are cultured in the presence of the ROCK inhibitor for at least 3 days.

9. The process according to claim 1, which comprises the following steps:
a) isolating a hair follicle in the telogen phase from a scalp sample;
b) separating the germ cells from the connective tissue sheath of the hair follicle;
c) depositing the germ cells on a feeder support 3T3 fibroblasts that has been treated with mitomycin, in a culture medium;
d) amplifying the germ cells into to obtain keratinocytes positive for CD200, CD29 and K15 markers at the surface of said support in the presence of a ROCK inhibitor;
e) recovering the keratinocytes positives for the CD200, CD29 and K15 markers; and
f) culturing the keratinocytes obtained in step e) in a 3D culture with connective tissue sheath fibroblasts and/or dermal papilla fibroblasts to allow their differentiation into the tubular structure.

10. The process according to claim 9, in which the said keratinocytes positives for the CD200, CD29 and K15 markers are recovered when they reach confluence while forming clusters.

11. The process according to claim 9, wherein in the step f), the number of keratinocytes placed in culture is between 1000 and 4000 cells per cm$^2$.

12. The process according to claim 9, which comprises isolating the hair follicle in the telogen phase from the scalp sample by microdissection and further comprises between steps b) and c) separating the germ cells from the connective tissue and dermal part of the dermal papilla and culturing only the germ cells.

* * * * *